(12) United States Patent
Goto et al.

(10) Patent No.: US 6,891,963 B1
(45) Date of Patent: May 10, 2005

(54) IMAGE DISPLAY

(75) Inventors: Yoshihiro Goto, Tokyo (JP); Hiroshi Takagi, Kashiwa (JP); Dai Shinohara, Kitasoma-gun (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/869,760

(22) PCT Filed: Jan. 5, 2000

(86) PCT No.: PCT/JP00/00016

§ 371 (c)(1),
(2), (4) Date: Jul. 5, 2001

(87) PCT Pub. No.: WO00/41132

PCT Pub. Date: Jul. 13, 2000

(30) Foreign Application Priority Data

Jan. 6, 1999 (JP) .......................................... 11-001320

(51) Int. Cl.[7] ................................................ G06K 9/00
(52) U.S. Cl. ........................ 382/131; 345/419; 345/424; 382/130; 382/285; 382/294; 600/410; 600/424; 600/425; 600/443
(58) Field of Search ................................ 345/419, 424; 378/4, 21; 382/130, 131, 132, 285, 294; 600/407, 410, 424, 425, 426, 414, 443

(56) References Cited

U.S. PATENT DOCUMENTS

| | | | | |
|---|---|---|---|---|
| 5,371,778 A | * | 12/1994 | Yanof et al. .................... | 378/4 |
| 5,454,371 A | * | 10/1995 | Fenster et al. ............... | 600/443 |
| RE35,798 E | * | 5/1998 | Kimura ....................... | 345/424 |
| 5,776,064 A | * | 7/1998 | Kalfas et al. ................ | 600/141 |
| 5,825,908 A | * | 10/1998 | Pieper et al. ............... | 382/131 |
| 5,891,030 A | * | 4/1999 | Johnson et al. ............. | 600/407 |
| 6,064,904 A | * | 5/2000 | Yanof et al. ................. | 600/414 |
| 6,266,453 B1 | * | 7/2001 | Hibbard et al. ............. | 382/294 |
| 6,301,497 B1 | * | 10/2001 | Neustadter .................. | 600/410 |
| 6,341,231 B1 | * | 1/2002 | Ferre et al. ................. | 600/424 |
| 6,377,839 B1 | * | 4/2002 | Kalfas et al. ............... | 600/426 |
| 6,529,758 B2 | * | 3/2003 | Shahidi ....................... | 600/407 |
| 6,754,374 B1 | * | 6/2004 | Miller et al. ................ | 382/128 |

\* cited by examiner

*Primary Examiner*—Bhavesh M. Mehta
*Assistant Examiner*—Gregory Desire
(74) *Attorney, Agent, or Firm*—Antonelli, Terry, Stout & Kraus, LLP

(57) ABSTRACT

In an image display apparatus capable of storing therein a small amount of images and also capable of displaying two sorts, or more of images within a short time period, an axial image 1, a sagittal image 2, and a coronal image 3, which are loaded from a magnetic disk, are displayed on a CRT monitor 117. Image position indication FIGS. 4, 5, 6 are indicated above the respective tomographic images, and positions of the respective tomographic images are indicated on the respective image position indication FIGS. 4, 5, 6 by employing heavy lines 4a, 5a, 6a, and triangular symbols 4b, 5b, 6b. The positions of the tomographic images can be adjusted by dragging the respective triangular symbols 4b, 5b, 6b by using a mouse 118. Image position input FIGS. 7, 8, 9 are indicated under the respective tomographic images, and the positions of the respective displayed tomographic images are indicated on the image position input FIGS. 7, 8, 9 by way of drag bars 7a, 8a, 9a. Alternatively, the positions of the tomographic images may be adjusted by dragging the drag bars 7a, 8a, 9a by using the mouse 118.

12 Claims, 14 Drawing Sheets

IMAGE DISPLAY

TECHNICAL FIELD

The present invention is related to an image display apparatus capable of displaying thereon such an image by irradiating cone-shaped X-ray beams to an object under examination, and for acquiring transmission X-rays as projection data by way of a two-dimensional sensor along multiple directions so as to reconstruct tomographic images and the like (will be referred to as "cone-beam reconstruction" hereinafter). More specifically, the present invention is directed to such an image display apparatus capable of displaying thereon a tomographic image (sagittal image), another tomographic image (sagittal image), or another tomographic image (coronal image), which are cone-beam-reconstructed by a CT apparatus, the axial image being acquired along a vertical direction with respect to a body axis of an object under examination, the sagittal image being acquired along a parallel direction with respect to the body axis of the object under examination and also along a direction from a front surface of the object under examination to a rear surface thereof, and the coronal image being acquired along the parallel direction with respect to the body axis of the object under examination and also along a direction of a side surface of the object under examination.

BACKGROUND ART

An axial image, a sagittal image, or a coronal image, which are cone-beam-reconstructed by a CT apparatus, are displayed on a CRT monitor in an image display apparatus.

In a conventional image display apparatus, for instance, while only an axial image is stored in a magnetic disk, when the axial image is displayed, the axial image is read out from the magnetic disk to be displayed, whereas when a sagittal image and a coronal image are displayed, these sagittal and coronal images are reconstructed based upon the saved axial image to display the reconstructed sagittal/coronal images.

However, in the conventional image display apparatus, since a very large number of axial images are obtained by way of the cone-beam reconstruction, there is such a problem that while this very large number of axial images, and both the sagittal images and the coronal images which are obtained from the axial images are displayed on the monitor, searching of a desirable diagnostic portion may constitute very hard works with respect to operators.

Also, in order to form one sheet of such a sagittal image and one sheet of such a coronal image, all of the axial images are necessarily required. Thus, there is another problem that lengthy time is required so as to read out all of these axial images from the magnetic disk and to load the read axial images on the main memory.

To shorten the above-described readout time, such a method is conceivable. That is, while all of the three sorts of images are formed and the formed images are saved in the magnetic disk, only such an image to be displayed may be read out. However, this conceivable method requires the storage capacity of the magnetic disk which is three times larger than that of the above-explained method, resulting in a not-preferable method.

Also, there is such a need that an operator designates an effective region of data of a three-dimensional image so as to reduce an amount of data to be processed. As a result, the operator wants to display the images in a high speed.

Also, when an image is displayed, it is not easy to selectively determine that which image among the above-explained three sorts of images is displayed.

DISCLOSURE OF THE INVENTION

The present invention has been made to solve the above-explained problems, and therefore, has a first object to provide an image display apparatus capable of searching a desirable diagnostic portion in a high efficiency from any one of three sorts of images, i.e., a large number of axial images, sagittal images, and coronal images, which are obtained by way of the cone-beam reconstruction.

The present invention has a second object to provide an image display apparatus capable of displaying two sorts, or more of tomographic images within a short time period, which are intersected essentially perpendicular to each other, while any one of the stored images is less than other images.

To achieve the above-explained objects, an image display apparatus, according to the present invention, is featured by such an image display apparatus for displaying thereon two sorts, or more of images which are intersected essentially perpendicular to each other within a three-dimensional original image, comprising: image position designating means for designating image positions of the two sorts, or more of images within the three-dimensional original image; image position display means for displaying thereon figures indicative of the positions of the two sorts, or more of images within the three-dimensional original image, which are designated by the image position designating means; and image display means for displaying thereon at least one image among the two sorts, or more of images within the three-dimensional original image in relation to the figure.

In accordance with the present invention, the image position designating means designates the image positions of the two sorts, or more of images within the three-dimensional original image, respectively. The image position display means displays thereon the figures indicative of the positions of the two sorts, or more of images within the three-dimensional original image, which are designated by the image position designating means, respectively. The image display means displays thereon at least one image among the two sorts, or more of images within the three-dimensional original image in relation to the figure displayed by the image position display means. As explained above, since the image is displayed in connection with the figures indicative of the image display position designated by the image position display means, the position of the image under display can be grasped in relation to the three-dimensional original image, and also the desirable image can be displayed.

Also, to achieve the above-explained objects, an image display apparatus, according to the present invention, is featured by such an image display apparatus for selecting any of three-sorts of images which are intersected essentially perpendicular to each other within a three-dimensional original image, and for displaying thereon the selected image, comprising: image position designating means for designating any of the three sorts of images within the three-dimensional original image, and for designating an image position of the designated image within the three-dimensional original image; image position display means for displaying a figure indicative of the image position within the three-dimensional original image, which is designated by the image position designating means; and image display means for displaying an image within the three-dimensional original image in relation to the figure which indicates the image display position displayed by the image position display means.

In accordance with the present invention, the image position designating means designates any of the three sorts of images within the three-dimensional original image, and also designates the image position of the designated image within the three-dimensional original image. The image position display means displays the figure indicative of the image position within the three-dimensional original image, which is designated by the image position designating means, and the image display means displays the image within the three-dimensional original image in relation to the figure which indicates the image display position displayed by the image position display means. As explained above, since the image is displayed in relation to the figure indicative of the image display position displayed by the image position display means, both the sort of the image under display and the position thereof can be grasped in relation to the three-dimensional original image, and the desirable image can be displayed.

Also, to achieve the objects, an image display apparatus, according to the present invention, is featured by such an image display apparatus in which while a three-dimensional original image is produced by stacking a large number of tomographic images which are cone-beam-reconstructed, three sorts of 3-dimensional original images are stored in which the stacking directions of the large number of tomographic images are intersected essentially perpendicular to each other, and an image is displayed based upon the three sorts of 3-dimensional original images, comprising: image saving means for saving thereinto only data with in a region of a polyhedron which is internally contacted to a region used to reconstruct a tomographic image; and display means for displaying the three sorts of the 3-dimensional original image saved in this saving means.

Also, in accordance with the present invention, while the image saving means sets, for instance, two planes opposite to each other of a polyhedron, for example, a cube which is internally contacted to a three-dimensional original image among the three sorts of three-dimensional original images as a saving rage, and stores only the three sorts of three-dimensional original images between the two planes. The image saving means sets such the three-dimensional original image as the normal display subject, which is located between the two planes opposite to each other of the cube.

As previously explained, only such three-sorts of the three-dimensional original images are saved and used as the normal display subjects, which are located between the two planes opposite to each other of the cube which is internally contacted to the three-dimensional original images. As a result, the three-dimensional original images corresponding to the normal display subjects can be displayed in a short time period, while using a small amount of the saved images. The interval of these two planes located opposite to each other can be freely changed by an operator by using a mouse and the like.

As previously explained, in accordance with the present invention, since at least one image among two sorts, or more of the images is displayed in relation to the figure indicative of the image display position displayed by the image position display means, the position of the image under display can be grasped in relation to the three-dimensional original image, and the desirable image can be displayed.

Also, in accordance with the present invention, any one of the three sorts of images is displayed in relation to the figure indicative of the image display position displayed by the image position display means, the position and also the sort of the image under display can be grasped in relation to the three-dimensional original image, and the desirable image can be displayed.

As a consequence, a desirable diagnostic portion can be searched in a high efficiency from any one of the three sorts of images which are made of large amounts of data, and are acquired by employing the cone-beam reconstruction.

Also, in accordance with the present invention, only such three-sorts of the three-dimensional original images are saved and used as the normal display subjects, which are located between the two planes opposite to each other of the polyhedron which is internally contacted to the three-dimensional original images. As a result, the three-dimensional original images corresponding to the normal display subjects can be displayed in a short time period, while using a small amount of the saved images.

BEST MODE FOR CARRYING OUT THE INVENTION

Various preferable embodiment modes of an image display apparatus according to the present invention will now be described in detail with reference to the accompanying drawings.

Figure 1:
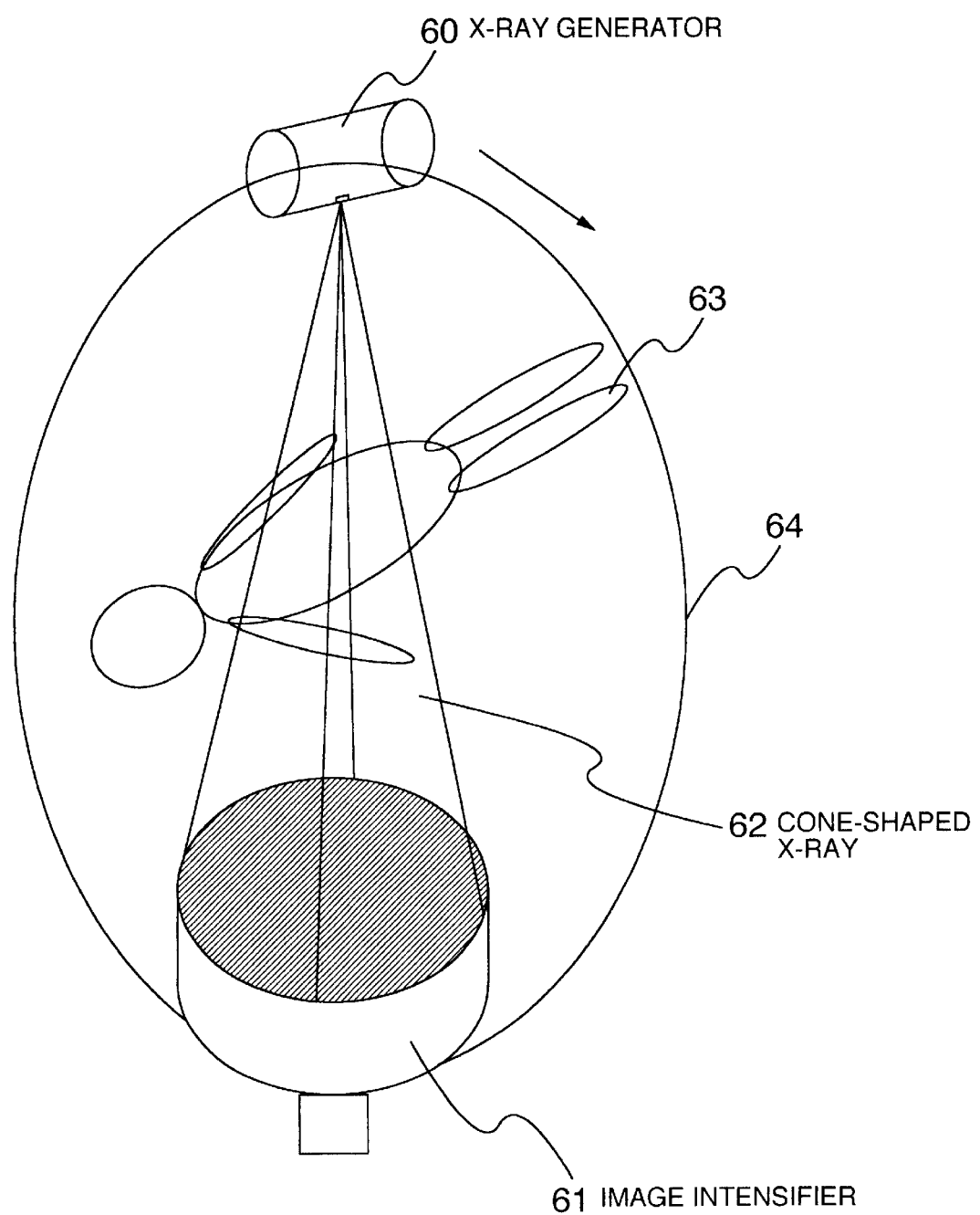
FIG. 1 is an explanatory diagram for indicating an arrangement of an X-ray CT apparatus to which an image display apparatus of the present invention is applied.

FIG. 1 is an explanatory diagram for indicating an arrangement of an X-ray CT apparatus to which an image processing apparatus of the present invention is applied. A cone-shaped X-ray 62 generated from an X-ray generator 60 penetrates, or passes through an object under examination 63, and a transmission X-ray is entered into a circular image intensifier 61 which is provided opposite to the X-ray generator 60 so as to detect an amount of the transmission X-ray. The detected transmission X-ray amount is converted into an electric signal to obtain projection data. A tomographic image is obtained by processing the projection data.

Figure 2:
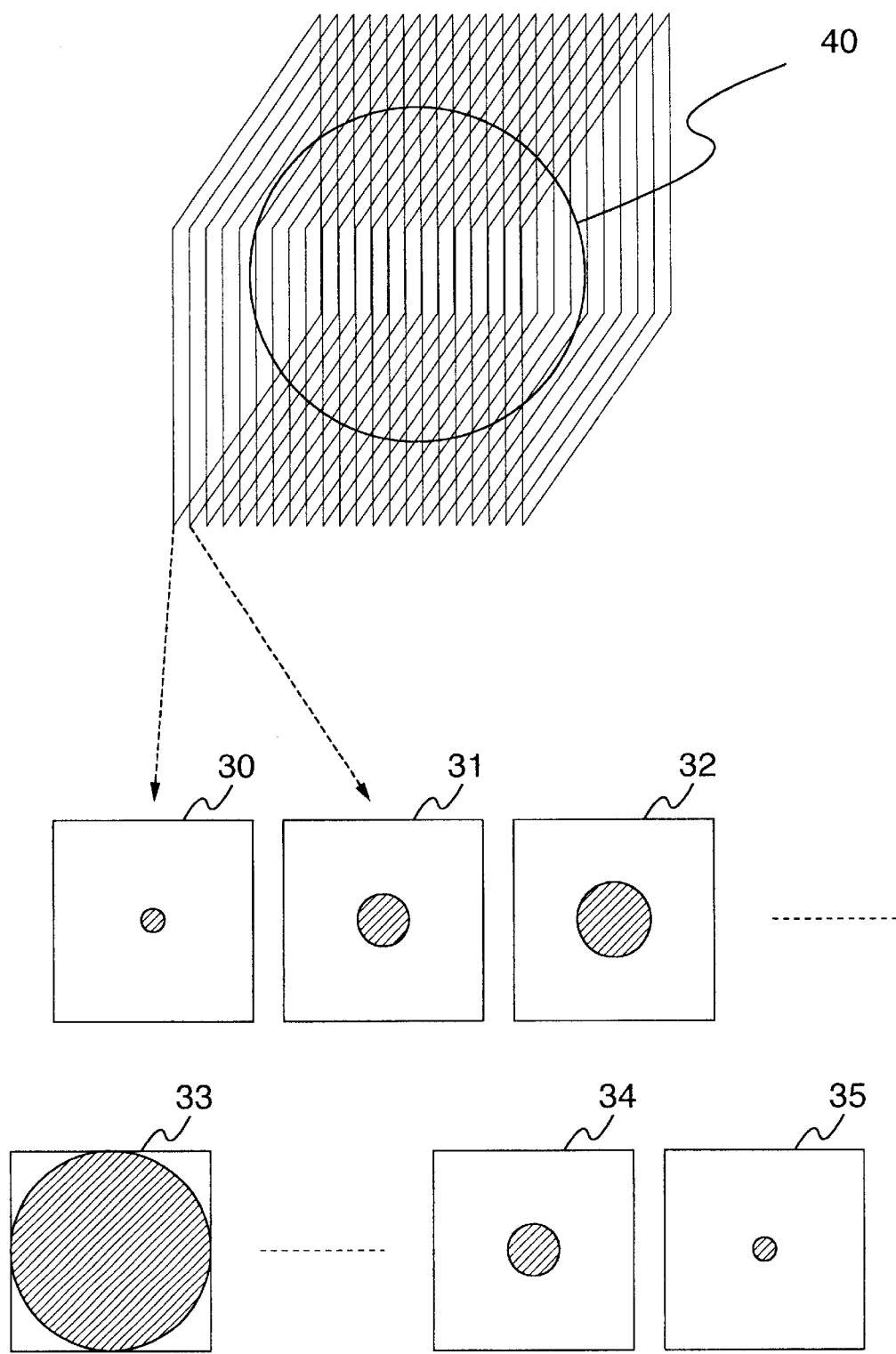
FIG. 2 is an explanatory diagram for showing both an effective region and a tomographic image.

Both the X-ray generator 60 and the image intensifier 61 are rotated around an orbit 64 located around the object under examination 63. Since the X-ray generator 60 and the image intensifier 61 are rotated by 1 turn, several hundreds of tomographic images 30, 31, 32, ---, 33, ---, 34, and 35 as indicated in FIG. 2 are cone-beam-reconstructed.

Since the above-explained image intensifier 61 is the circular shape, an effective regions 40 which is reconstructed becomes a spherical shape. A region which is surrounded by an inclined line among each of the tomographic images 30, ---, 35 indicates one sectional plane of the effective region 40.

Figure 3A:
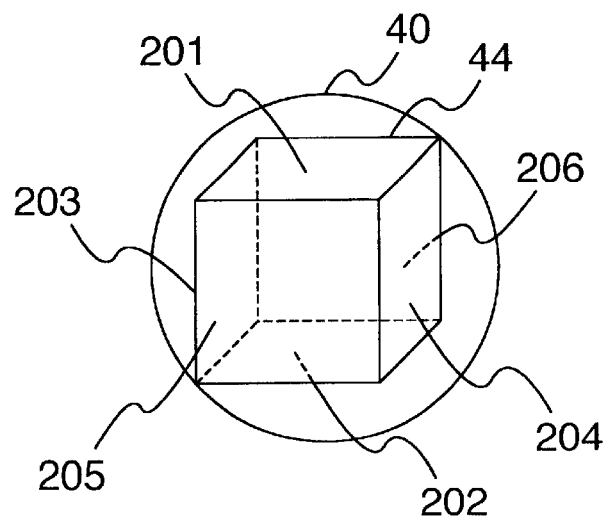
FIG. 3A and FIG. 3B are explanatory diagrams for describing a selection method of tomographic images to be saved.
Figure 3B:
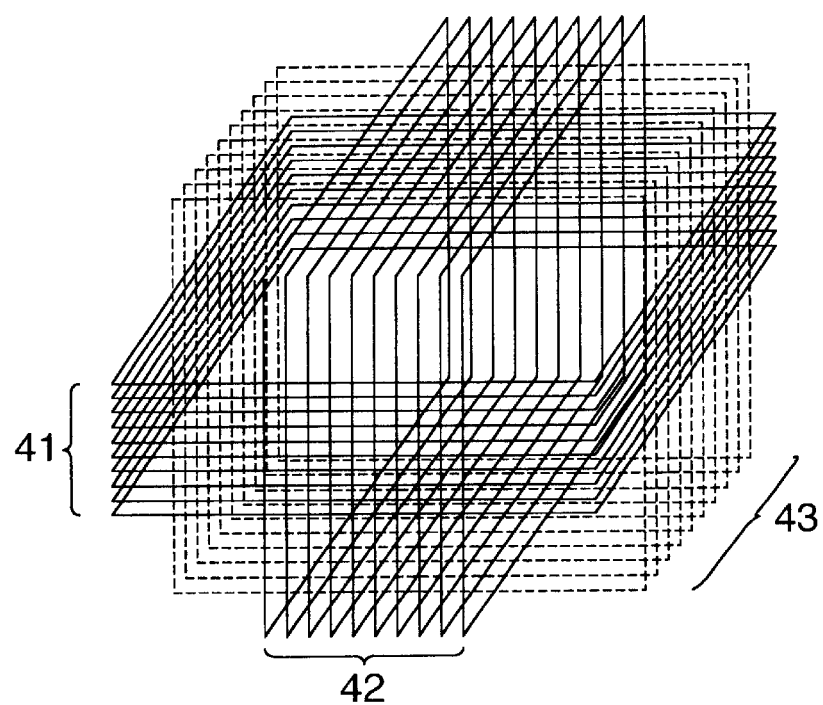

When all of three sorts of images which are intersected perpendicular to each other are saved, since a required storage capacity is largely increased, a polyhedron (for instance, a cube 44) is set in accordance with the present invention. As indicated in FIG. 3A and FIG. 3B, the polyhedron is internally contacted to the effective region 40. Then, only such a tomographic image between two planes of this cube 44 is saved, or stored in a magnetic disk. The two planes are located opposite to each other. In this case, since such an example that the three sorts of images are intersected perpendicular to each other may be best understood, this example will be exemplified. It should be noted that this exemplified example may involve such a case that these images are intersected essentially perpendicular to each other. In other words, only the below-mentioned tomographic images are saved, namely, tomographic images 41, 41, ---, between an upper surface 201 of the cube 44 and a bottom surface 202 thereof; tomographic images 42, 42, ---, between side surfaces 203 and 204 of the cube 44; and tomographic images 43, 43, ---, between a front surface 205 and a rear surface 206 of the cube 44. Since these saved tomographic images are read out from the magnetic disk, a desirable tomographic image can be displayed. As a consequence, the three sorts of tomographic images may be displayed within a short time period with a small amount of the saved images, while a large amount of images are not read.

Figure 4:
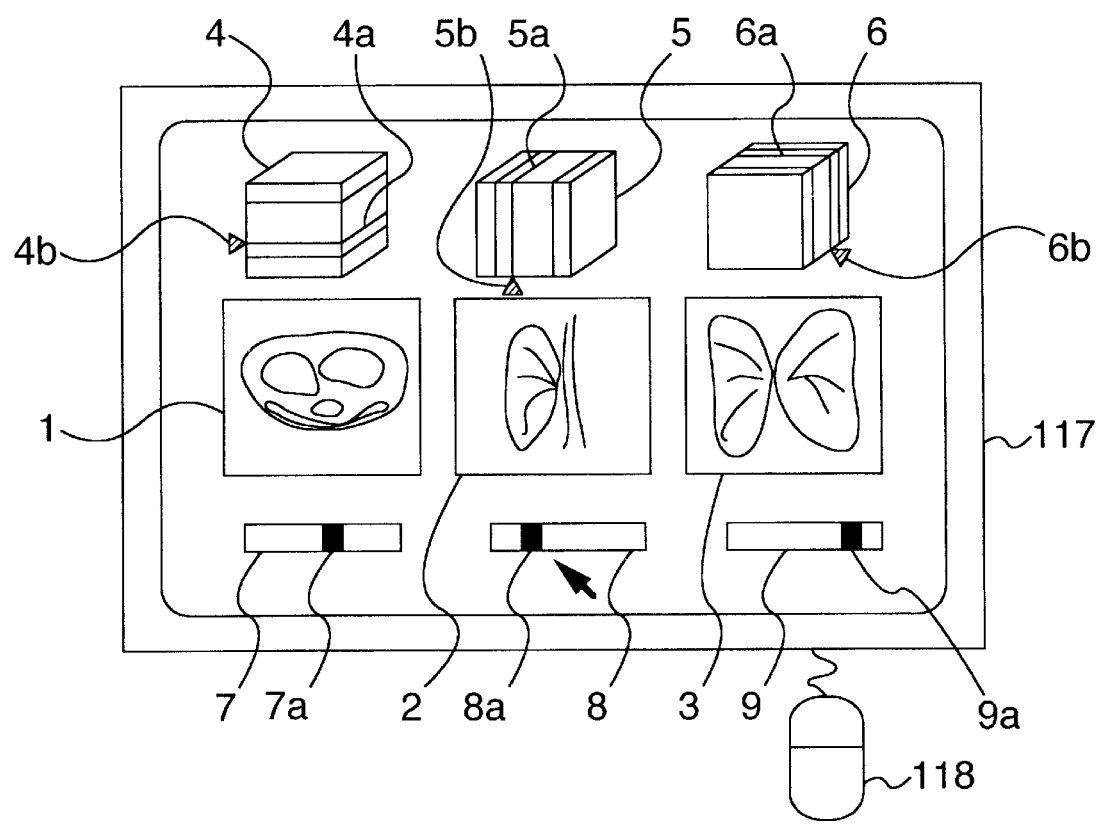
FIG. 4 is an explanatory diagram for showing a CRT monitor used to display thereon a tomographic image.

FIG. 4 is an explanatory diagram for indicating a CRT monitor 117 on which a tomographic image is displayed.

Figure 5:
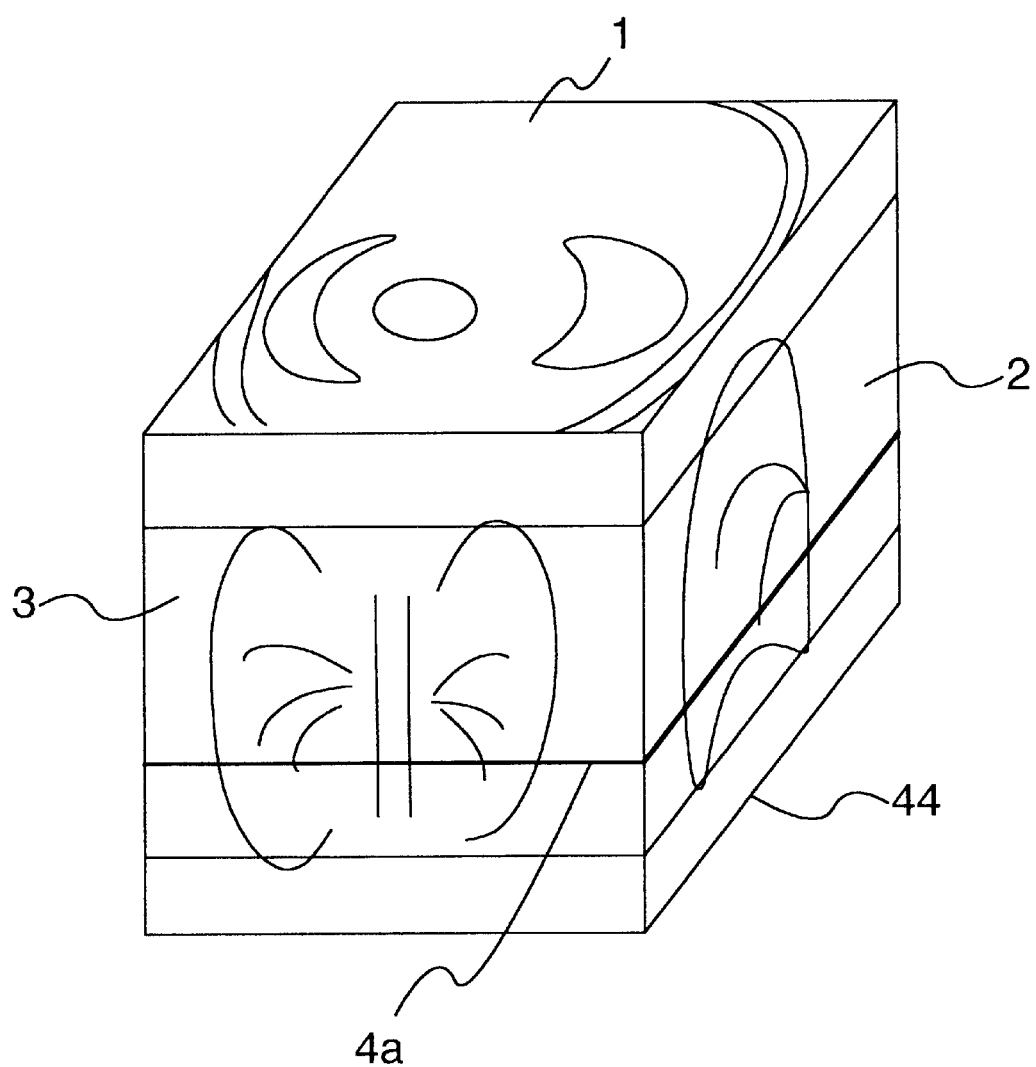
FIG. 5 is an explanatory diagram for indicating a rectangular solid which represents three sorts of tomographic images.
Figure 6:
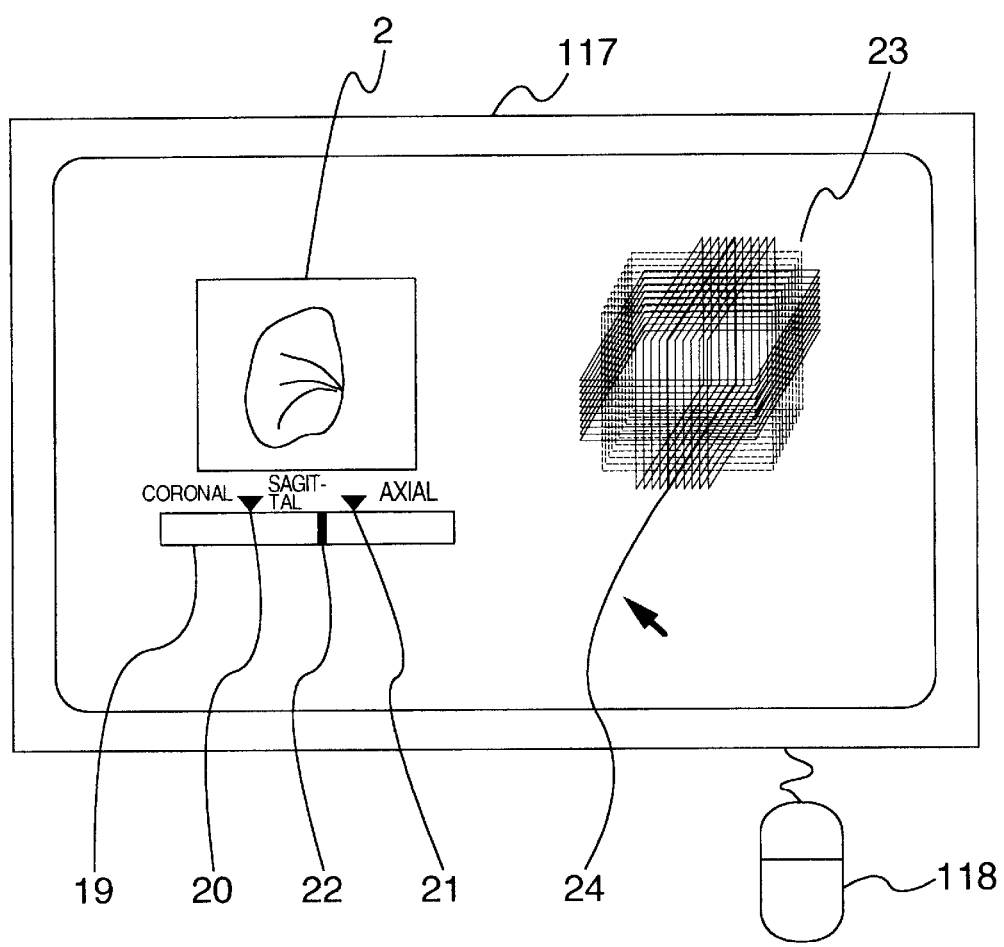
FIG. 6 is an explanatory diagram for showing a CRT monitor which selectively displays thereon three sorts of tomographic images.

On this CRT monitor 117, an axial image 1, a sagittal image 2, and a coronal image 3 are displayed which are read out from the magnetic disk. Image position indication FIGS. 4, 5, 6 are displayed above the respective tomographic images. Positions of the respective displayed tomographic images are represented by heavy lines 4a, 5a, 6a, and triangular symbols 4b, 5b, 6b on the respective image position indication FIGS. 4, 5, 6. A position of a displayed tomographic image may be adjusted by dragging each of the triangular symbols 4b, 5b, 6b by using a mouse 118. Also, the tomographic images of both the edges of the cube 44 are displayed on this image position indication FIGS. 4, 5, 6. While this tomographic image between the both edges is set as the normal display subject, other images are formed from either one image or the other image of two sorts of other images, and then are displayed.

Figure 7:
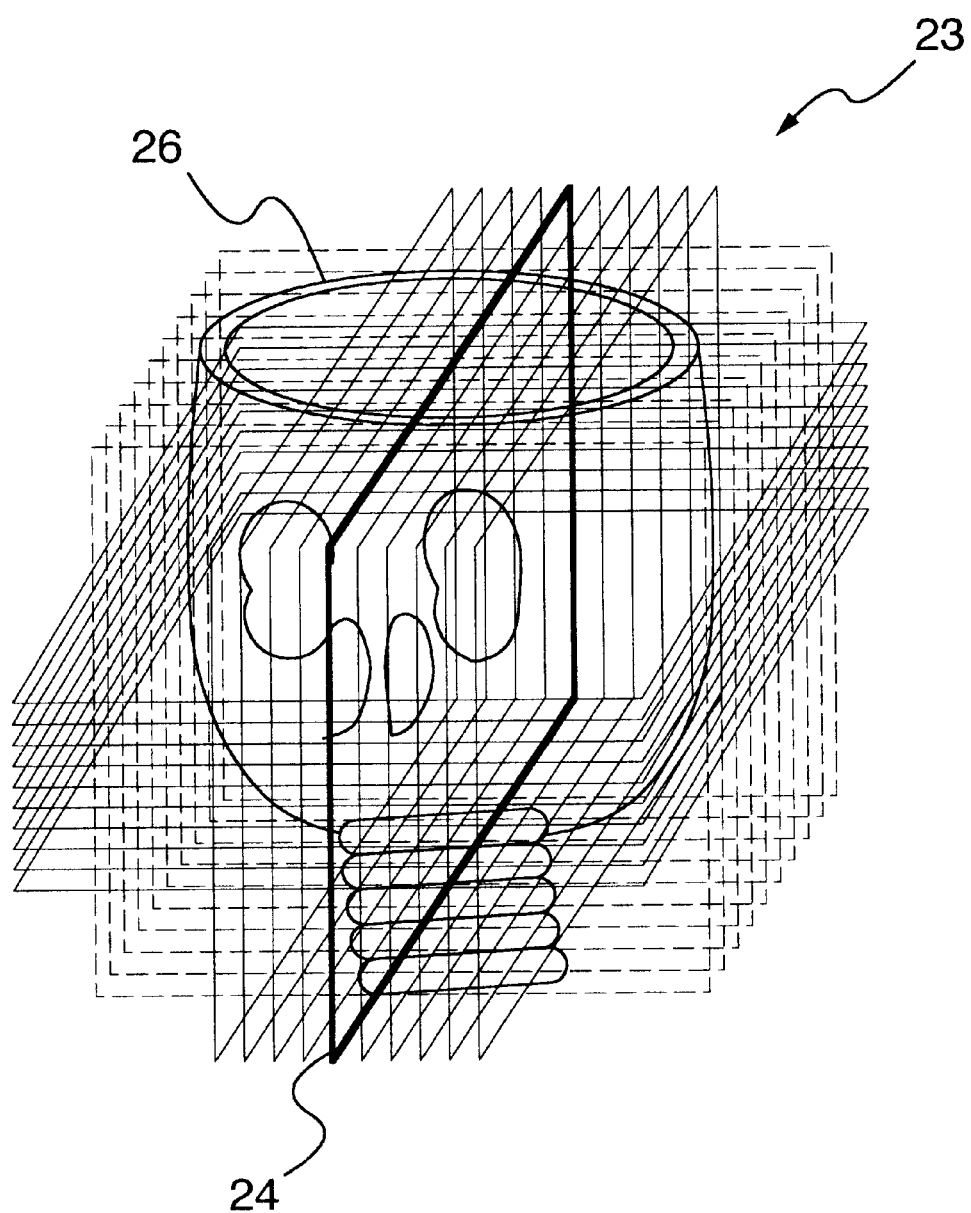
FIG. 7 is an explanatory diagram for indicating a method used to synthesize a three-dimensional image with a position indication image to display a synthesized three-dimensional image.
Figure 8:
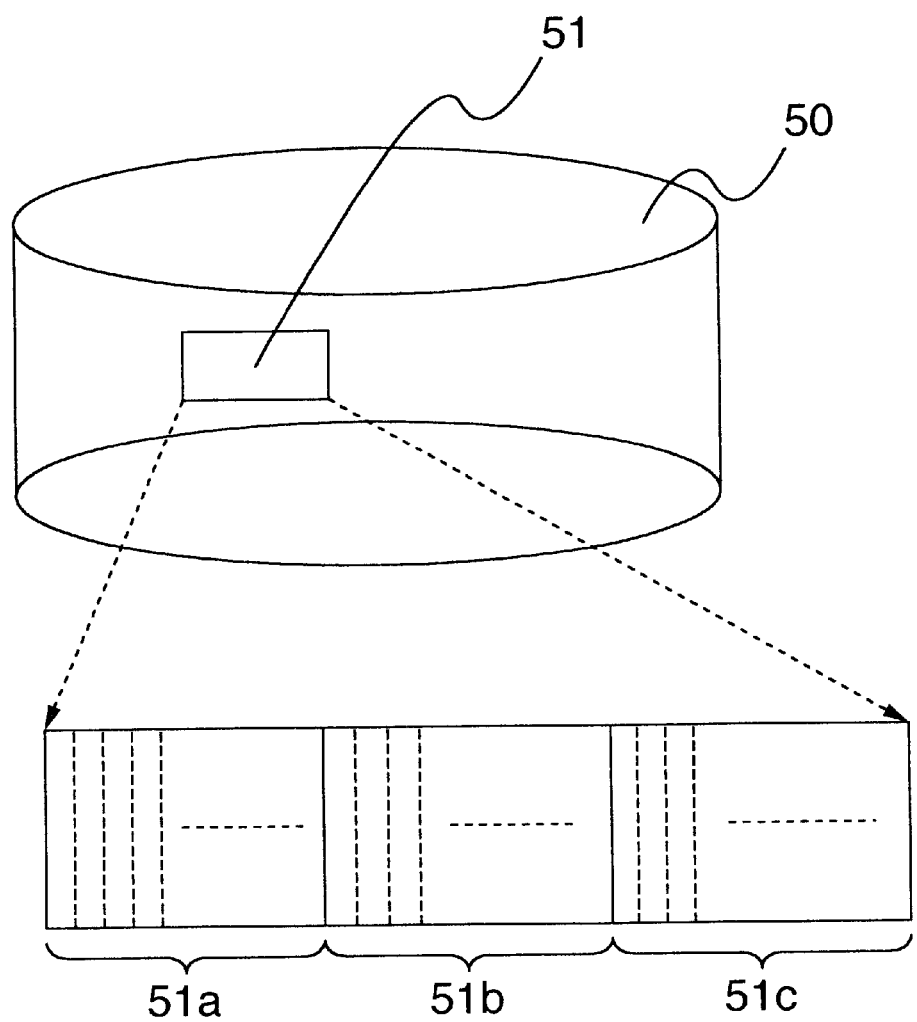
FIG. 8 is an explanatory diagram for indicating a region used to save three sorts of tomographic images.
Figure 9:
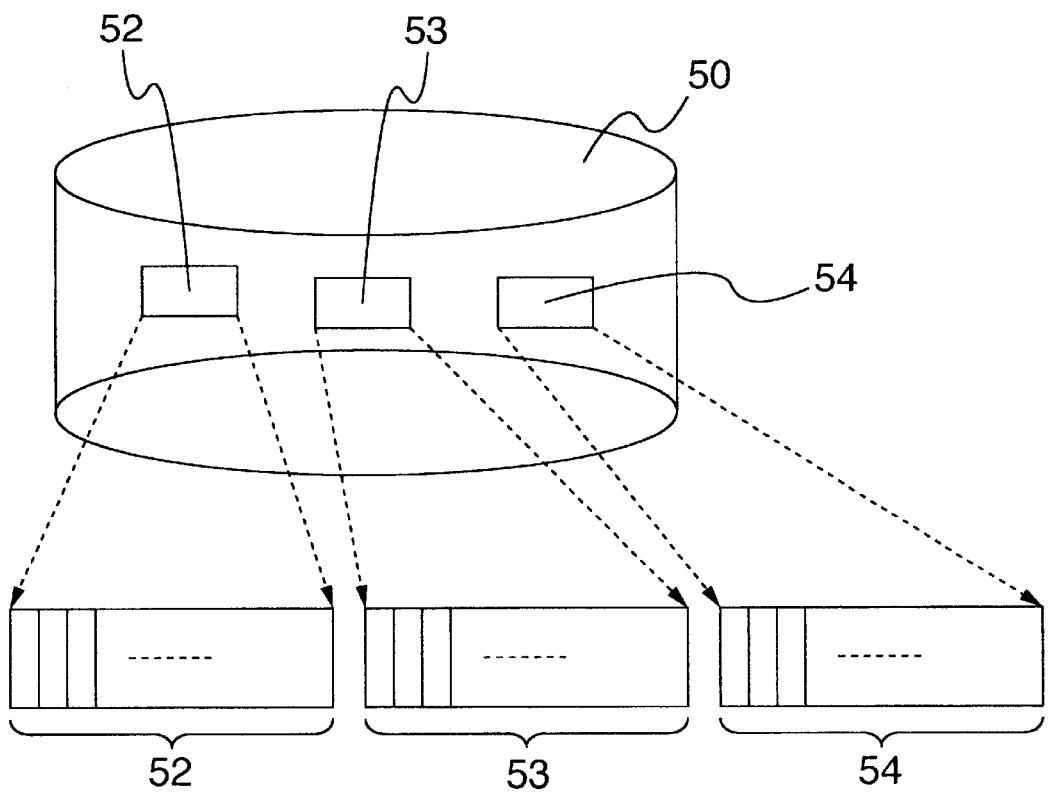
FIG. 9 is an explanatory diagram for showing a region used to save three sorts of tomographic images.

Also, while image position input FIGS. 7, 8, 9 are displayed below the respective tomographic images, positions of the respective displayed tomographic images are displayed by drag bars 7a, 8a, 9a on the image position input FIGS. 7, 8, 9. When the triangular symbols 4a, 5a, 6a of the image position indication FIGS. 4, 5, 6 are moved, the drag bars 7a, 8a, 9a are moved in connection thereto. Even when the drag bars 7a, 8a, 9a are dragged by the mouse 118, the positions of the tomographic images may be adjusted. It should be noted that in this embodiment, although both the image position indication FIGS. 4, 5, 6 and the drag bars 7a, 8a, 9a are displayed, any one of these figures and drag bars may be employed.

It should also be noted that the above-explained three sorts of tomographic images are displayed respectively in FIG. 4. As indicated in FIG. 5, alternatively, the axial image 1 may be displayed on the upper surface of the cube 44 of the image position indication FIGS. 4, 5, 6. Also, the sagittal image 2 may be displayed on the side surface of the cube 44, and the coronal image 3 may be displayed on the front surface thereof. FIG. 5 indicates such a case of the image position indication FIG. 4.

FIG. 6 is an explanatory diagram for indicating the CRT monitor 117 which displays only one tomographic image. Any one of the axial image 1, the sagittal image 2, and the coronal image 3, which are loaded from the magnetic disk, is displayed on this CRT monitor 117 (sagittal image 2 is displayed in this drawing). While an image position input FIG. 19 is displayed under the tomographic image, the position of the tomographic image may be adjusted by dragging a drag bar 22 by the mouse 118. Also, triangular symbols 20 and 21 are displayed on this image position input FIG. 19, and this image position input FIG. 19 is divided into three regions. A position of an axial image may be adjusted by a right region, a position of a sagittal image may be adjusted by a central region, and a position of a coronal image may be adjusted by a left region. Since the triangular symbols 20 and 21 cross over a region, a sort of a tomographic image to be displayed is automatically switched. The above-explained triangular symbols 20 and 21 constitute one example. Other methods may be employed. For instance, while the image position input FIG. 19 is divided by 3, the respective three-divided figures may clearly indicate the region of the axial image, the region of the sagittal image, and the region of the coronal image, respectively.

Also, an image position indication FIG. 23 is displayed on the right side of the tomographic image, and the position of the displayed tomographic image is indicated by a heavy line 24.

It should also be noted that as shown in FIG. 7, both the image position indication FIG. 23 and a three-dimensional image 26 may be synthesized with each other to display the synthesized image.

FIG. 8 is an explanatory diagram for indicating a saved region of a tomographic image. All of tomographic images are saved, or stored in a single file 51 of a magnetic disk 50. For instance, an axial image is saved in a region 51a of the file 51, a sagittal image is saved in a region 51b, and a coronal image is saved in a region 51c.

Also, as indicated in FIG. 9, an axial image may be saved in a file 52, a sagittal image may be saved in a file 53, and a coronal image may be saved in a file 54.

Figure 10:
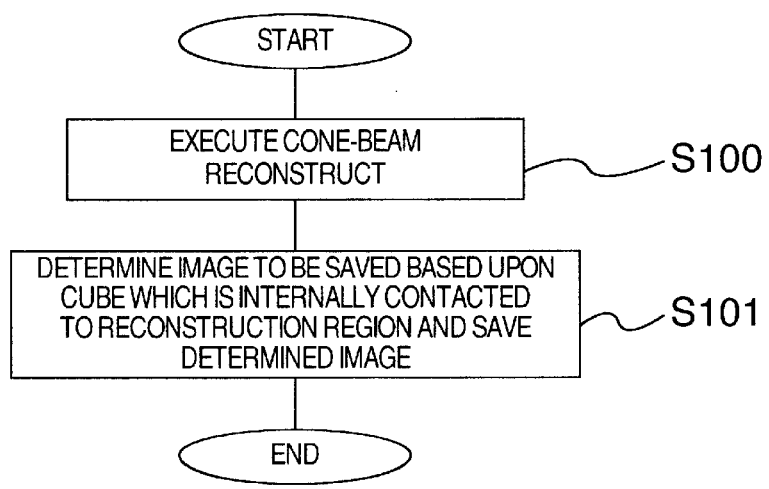
FIG. 10 is a flow chart for describing a saving sequential operation of a tomographic image.

FIG. 10 is a flow chart for describing a saving sequential operation of a tomographic image.

First, both the X-ray generator 60 and the image intensifier 61 are rotated on the orbit 64 located around the object under examination 63 in a constant time period to cone-beam-reconstruct several hundreds of the tomographic images 30, ---, 35 (step 100). Subsequently, only a tomographic image between two planes of a cube, which are located opposite to each other, is saved in the magnetic disk 50 (step 101). The cube is internally contacted to a reconstructed region.

Figure 11:
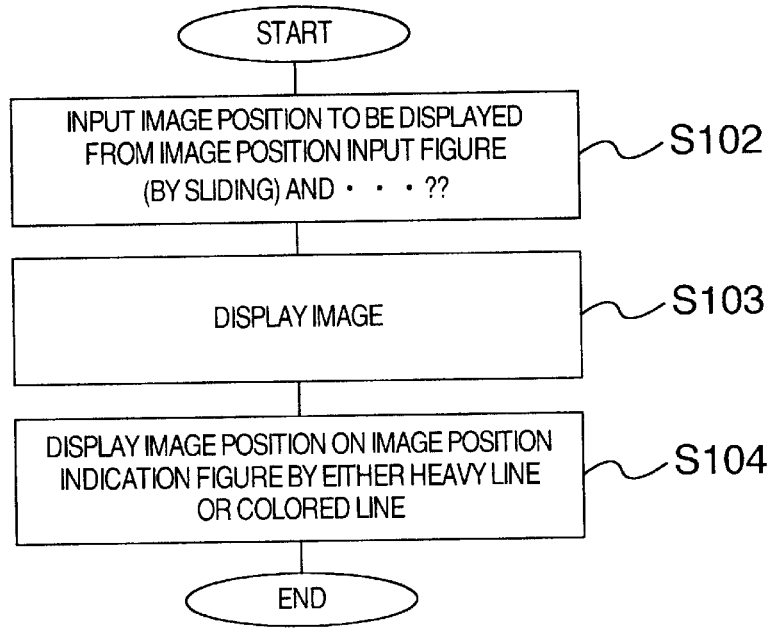
FIG. 11 is a flow chart for explaining a displaying sequential operation of a saved tomographic image.

FIG. 11 is a flow chart for showing a display sequential operation of a saved tomographic image.

First, as an initial value, an image of a specific position of each of an axial image, a sagittal image, and a coronal image is displayed.

In the image position input FIGS. 7, 8, 9 of the CRT monitor 117 shown in FIG. 4, a position of such a tomographic image which should be displayed is inputted by dragging the drag bars 7a, 8a, 9a by manipulating the mouse 118 (step 102).

The tomographic images 1, 2, 3 of the positions entered at the step 102 are indicated on the CRT monitor 117 (step 103). Also, the positions of the tomographic images 1, 2, 3 are indicated on the image position indication FIGS. 4, 5, 6 by way of color heavy lines 4a, 5a, 6a (step 104).

Figure 12:
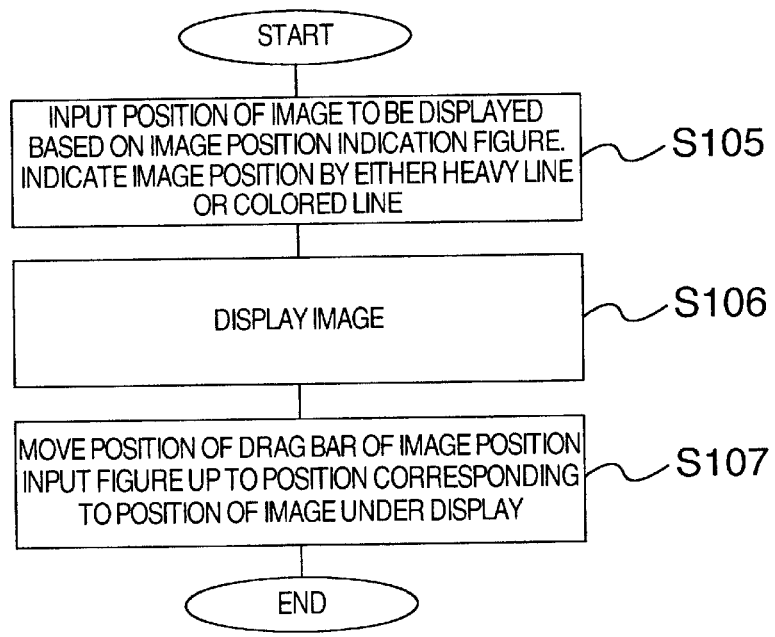
FIG. 12 is a flow chart for explaining a displaying sequential operation of a saved tomographic image.

FIG. 12 is a flow chart for describing a display sequential operation of a saved tomographic image, which is different from the method of FIG. 11.

First, as an initial value, an image of a specific position of each of an axial image, a sagittal image, and a coronal image is displayed.

A position of such a tomographic image which should be displayed is inputted by dragging the triangular symbols 4b, 5b, 6b of the image position indication FIGS. 4, 5, 6 of the CRT monitor 117 of FIG. 4 by using the mouse 118 (step 105). The image position may be indicated by a heavy line, or a colored line.

The tomographic images 1, 2, 3 of the positions entered at the step 105 are indicated on the CRT monitor 117 (step 106). Also, the drag bars 7a, 8a, 9a of the image position input FIGS. 7, 8, 9 are automatically moved up to the positions of the displayed tomographic images 1, 2, 3 (step 104).

Figure 13:
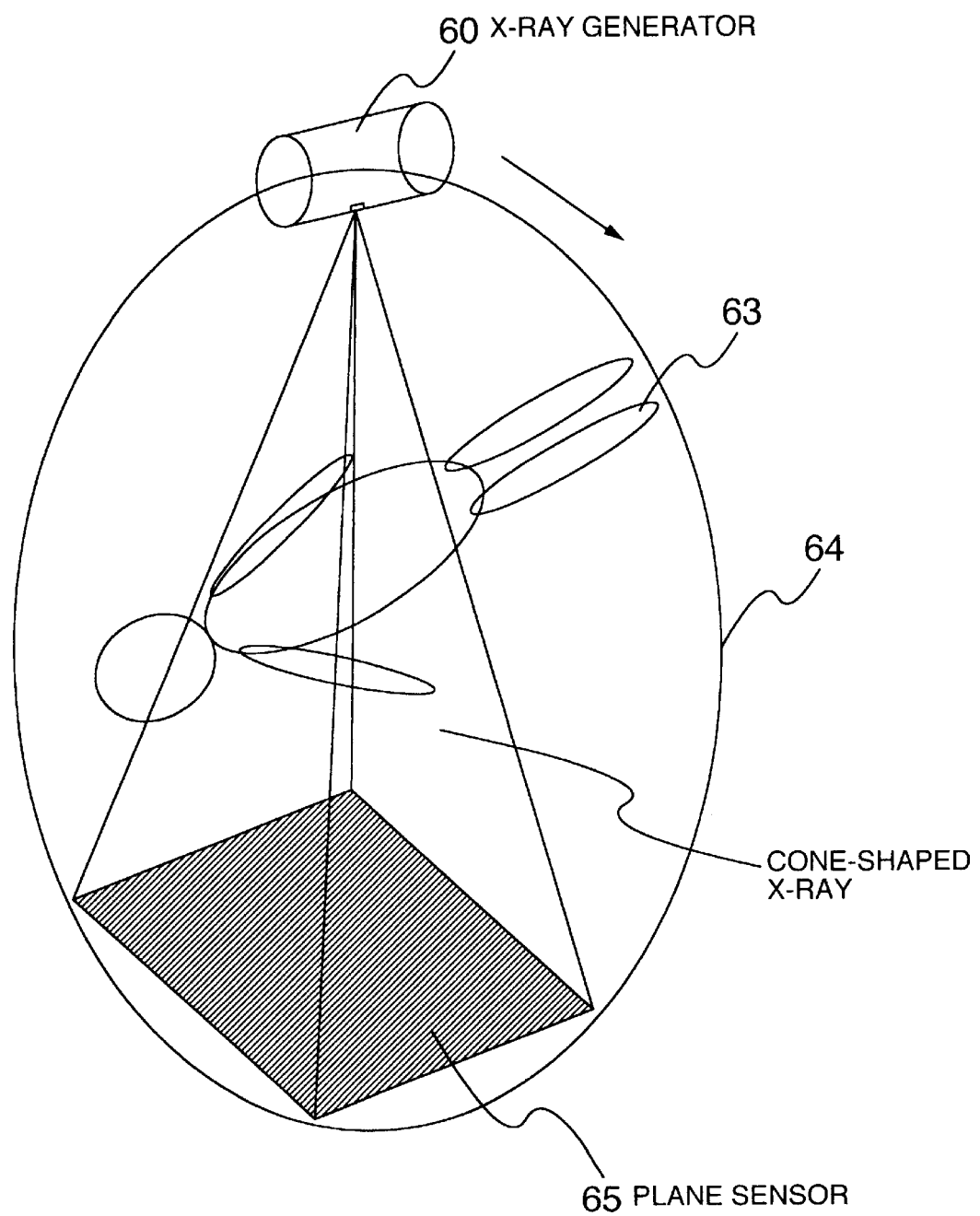
FIG. 13 is an explanatory diagram for showing an arrangement an X-ray CT apparatus using a plane sensor 65.
Figure 14:
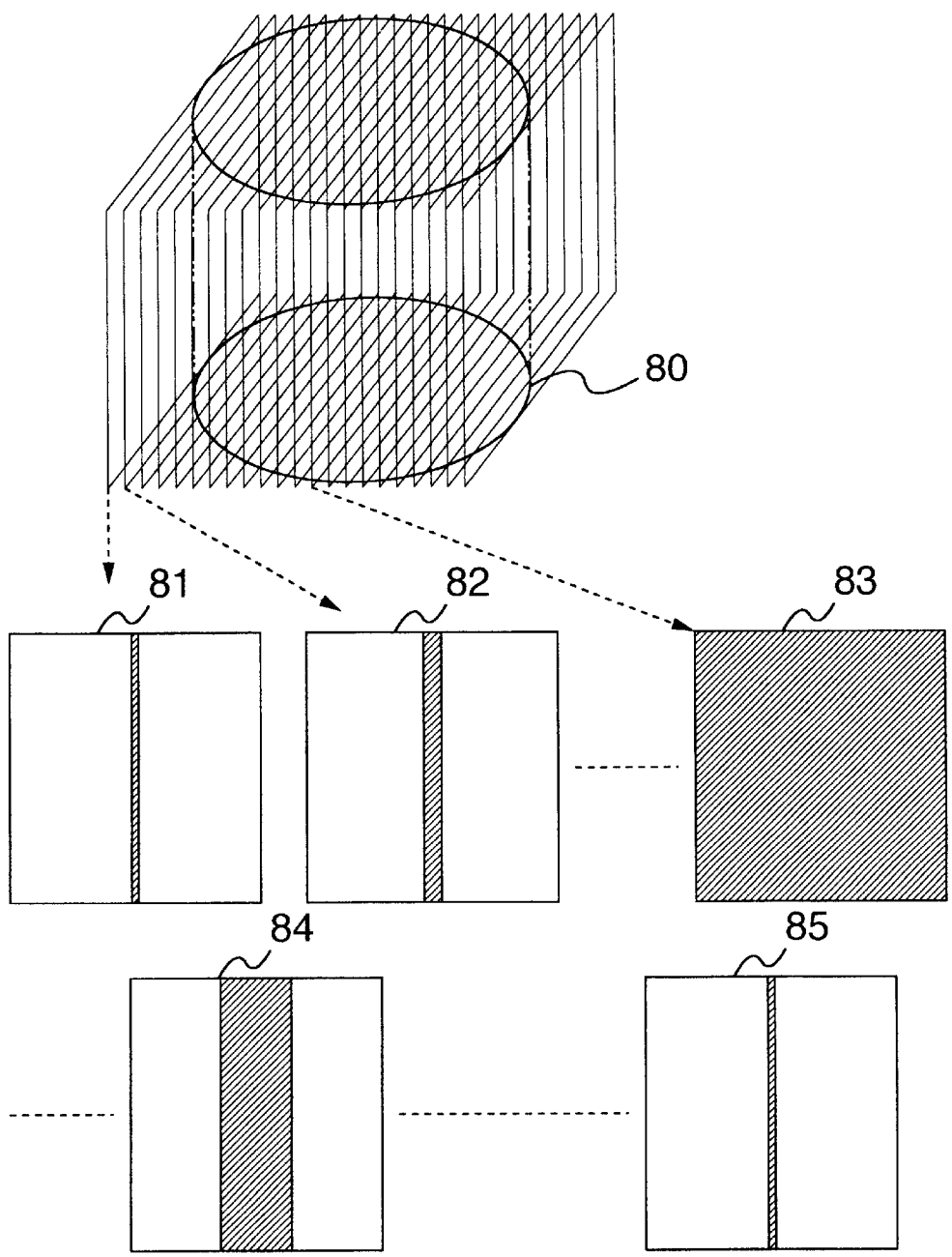
FIG. 14 is an explanatory diagram for representing both an effective region and a tomographic image in the X-ray CT apparatus of FIG. 13.

FIG. 13 is an explanatory diagram for indicating an arrangement of an X-ray CT apparatus which employs a plane sensor 65 instead of the image intensifier 61 of FIG. 1. Since the plane sensor 65 is a rectangular shape, such a cylindrical-shaped effective region 80 to be reconstructed as shown in FIG. 14 is formed. A region surrounded by an inclined line among the respective tomographic images 81, 82, ---, 83, ---, 84 and 85 indicates one sectional plane of the effective regions 80.

Figure 15A:
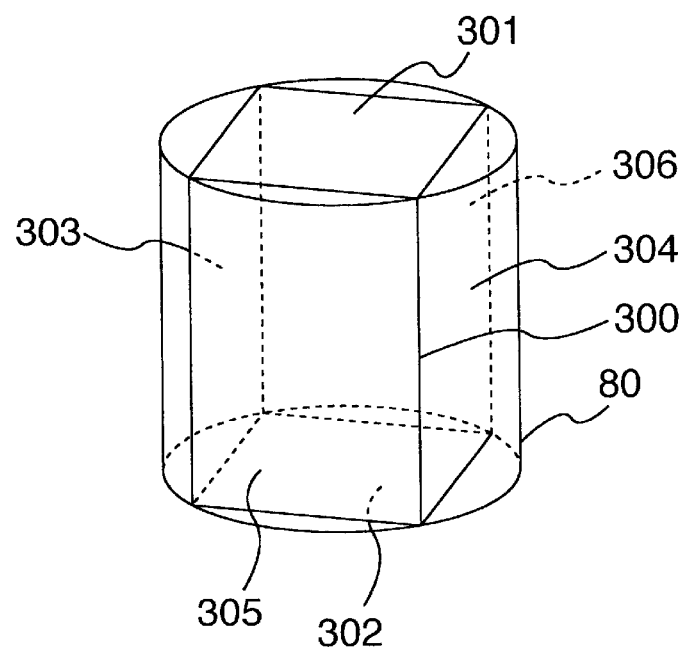
FIG. 15A and FIG. 15B are explanatory diagrams for explaining a method of selecting tomographic images saved in the X-ray CT apparatus of FIG. 13.
Figure 15B:
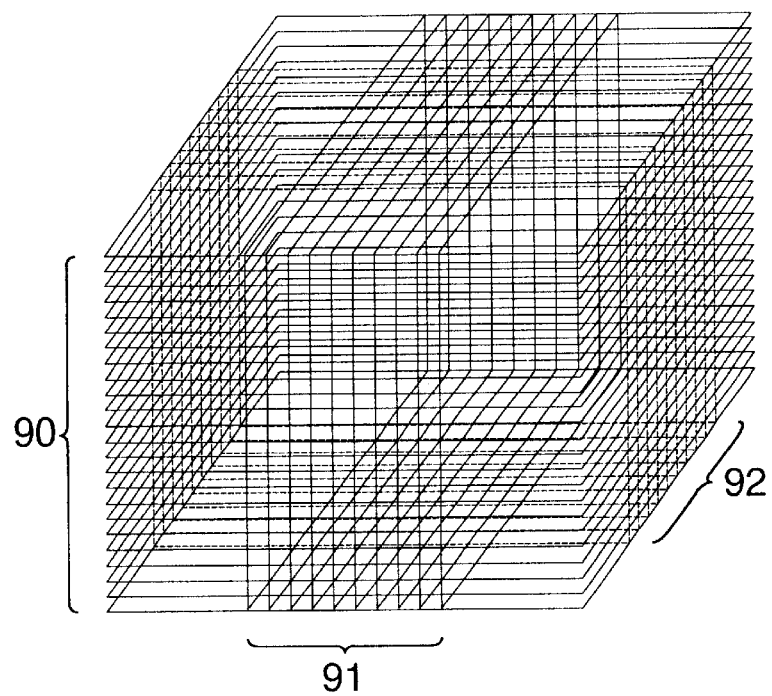

In the present invention, as represented in FIG. 15A, a rectangular solid 300 is set which is internally contacted to the effective region 80, and only a tomographic image between two planes of this rectangular solid 300, which are located opposite to each other, is saved in a magnetic disk. In other words, tomographic images 90, 90, ---, between an upper surface 301 of this rectangular solid and a bottom surface 302 thereof are saved. Only tomographic images 91, 91, ---, between side surfaces (303, 304) of this rectangular solid and saved, and only tomographic images 92, 92, ---, between a front surface 305 and a rear surface 306 of this rectangular solid are saved. A desirable tomographic image can be displayed by reading these saved tomographic images from the magnetic disk. As a result, the three sorts of tomographic images can be displayed within a short time period based upon a small amount of the saved images, while a large amount of images are not read out.

Figure 16:
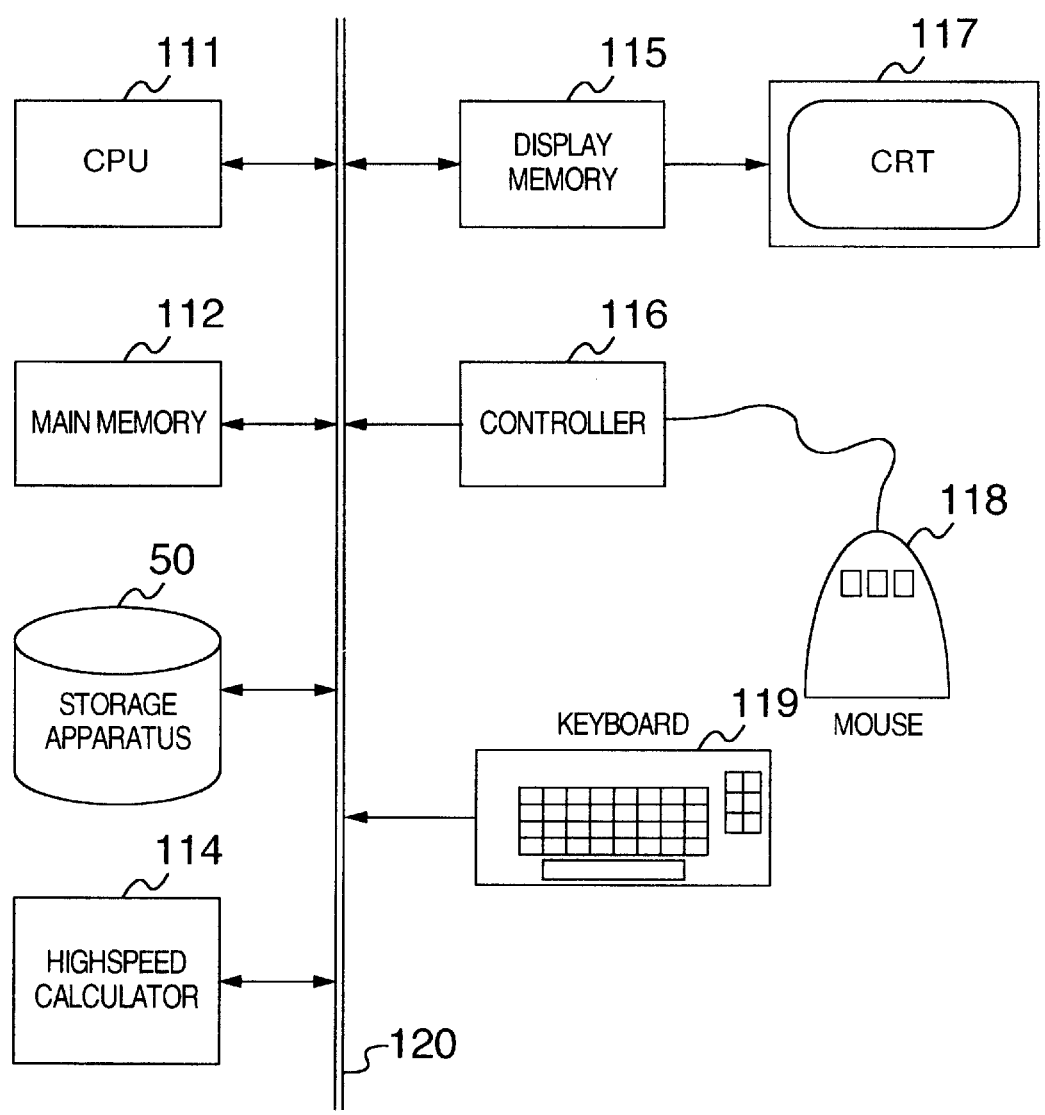
FIG. 16 is a block diagram for indicating a hardware structure of an image display apparatus.

FIG. 16 is a block diagram for indicating a hardware structure of an image display apparatus capable of reading the above-explained respective embodiments. This image display apparatus is to record and display medical image data which are acquired by using, for example, an X-ray CT apparatus with respect to a region of interest of an object under examination. The image display apparatus is arranged by a central processing unit (CPU) 111, a main memory 112, a high-speed calculator 114, a storage apparatus 50, a display memory 115, a CRT monitor 117, a mouse 118, a mouse controller 116, a keyboard 119, and a common bus 120. The central processing unit (CPU) 111 controls operations of the respective structural elements. The main memory 112 stores therein a control program of the image display apparatus. The high-speed calculator 114 executes various sorts of calculations. The storage apparatus 50 is constructed of a magnetic disk and a disk using optical information, into which a plurality of tomographic images and an image reconstruction program are stored. The display memory 115 stores thereinto reconstructed image data in order to display the reconstructed images. The CRT monitor 117 is provided as a display apparatus for displaying thereon the image data supplied from this display memory 115. The mouse 118 is provided as a position input apparatus. The mouse controller 116 detects a condition of the mouse 118 to output to the CPU 111, such a signal as to a position of a mouse pointer on the CRT 117 and the condition of the mouse 118. The keyboard 119 is employed so as to input various sorts of operation instructions. The common bus 120 is to connect the above-explained structural elements to each other.

The present invention is not limited to the above-explained embodiments, but may involve various sorts of modifications which are covered by a scope of claims.

INDUSTRIAL APPLICABILITY

The present invention can be utilized to various sorts of investigation apparatus such as a medical diagnose apparatus, an analysis apparatus, an amusement apparatus, and a baggage investigation apparatus of an air port, which require to reconstruct a necessary image from three sorts of 3-dimensional original images in which overlapping directions are essentially located perpendicular to each other.

What is claimed is:

1. An image display apparatus for displaying thereon two or more sorts of images which are intersected essentially perpendicular to each other within a three-dimensional original image of an object, comprising:

storing means for storing three-dimensional original image data;

figure display means for displaying figures for indication of positions of said two or more sorts of images displayed on the image display apparatus;

image position designating means for designating desired positions of desired images on said figures displayed by said figure display means;

image reading-out means for reading-out at least one image of said two or more sorts of images corresponding to said positions designated from said three-dimensional original image data; and image display means for displaying said at least one image read out by said image reading-out means and at least one figure corresponding to said image read out on the same screen, wherein said image displayed changes in synchronization with the position designated for said image displayed.

2. An image display apparatus according to claim 1, further comprising:

means for displaying said two or more sorts of images on the same given.

3. An image display apparatus according to claim 1, wherein said image display means displays at least two images read out by said image reading-out means and at least two figures corresponding respectively to said at least two images read out on the same screen, wherein each of said images displayed changes in synchronization with the position designated for each of said images displayed.

4. An image display apparatus according to claim 1, further comprising drag means for setting at least one drag bar indicative of positions of the at least one image read out by said image reading-out means and at least one drag bar corresponding to said image read out on the same screen, wherein said image display changes in synchronization with the position designated for said image displayed.

5. The image display apparatus according to claim 1, further comprising selection means for selecting a sort of image from three-sorts of images which are intersected essentially perpendicular to each other within said three-dimensional original image;

wherein said figure display means comprises means for displaying a figure for indication of a position of an image selected;

wherein said image position designating means comprises means for designating a position of said image selected on said figure displayed;

wherein said image reading-out means comprises means for reading-out an image corresponding to said position designated from said three-dimensional original image data; and wherein said image display means comprises means for displaying said image read out and said figure indicating said position of said image read out on the same screen.

6. An image display apparatus according to claim 5, further comprising:

means for synthesizing said figure within a three-dimensional image to display the synthesized image.

7. An image display apparatus for displaying thereon two or more sorts of images which are intersected essentially perpendicular to each other within a three-dimensional original image of an object, comprising:

storing means for storing three-dimensional original image data;

image position indication means for displaying bars for indication of positions of said two or more sorts of images;

drag means for setting drag bars indicative of positions of said two or more sorts of images to desired positions of desired images on said bars displayed;

image reading-out means for reading-out at least one sort of image of said two or more sorts of images from said three-dimensional original image data in synchronization with a position of said drag bar; and image display means for displaying at least one image read out by said image reading-out means and at least one bar corresponding to said image read out on the same screen, wherein said image displayed changes in synchronization with the position designated for said image displayed.

8. The image display apparatus according to claim 7, further comprising figure display means for displaying a figure for indication of position of each of said two or more sorts of images, said position being displayed in a three-dimensional manner;

wherein said image display means comprises means for displaying at least one image read by said image reading-out means and at least one of said bar corresponding to said image read out and said figure indicating said position of said image read out on the same screen.

9. An image display apparatus for displaying thereon three sorts of images which are intersected essentially perpendicular to each other within a three-dimensional original image of an object, comprising:

storing means for storing three-dimensional original image data;

image selection means for displaying a bar for selection of a sort of image and a position of an image to be displayed from said three sorts of images;

selection means for selecting a sort of image and a position of said sort of image selected on said bar by moving a drag bar;

image reading-out means for reading-out an image corresponding to said position selected from said three-dimensional original image data; and image display means for displaying said image read out by said image reading-out means and said bar on the same screen, wherein said image displayed changes in synchronization with the position selected for said image displayed.

10. The image display apparatus according to claim 9, further comprising figure creating means for creating a schematic figure in which said position of image selected is shown in a three-dimensional manner within tomographic images being schematically displayed, and wherein said image display means comprises means for displaying said schematic figure together with said image read out and said bar on the same screen, wherein the position of the schematic figure changes in synchronization with the position selected for said image displayed.

11. The image display apparatus according to claim 10, wherein said image display means comprises means for highlighting a part of said schematic figure, said part corresponding to said position of said image selected.

12. The image display apparatus according to claim 10, wherein said image display means comprises means for displaying a three-dimensional image in a overlapped manner on said schematic figure.

* * * * *